(12) United States Patent
Kunuki et al.

(10) Patent No.: US 7,611,905 B2
(45) Date of Patent: Nov. 3, 2009

(54) APPARATUS AND METHOD OF ASSAY IN UTILIZING ATTENUATED TOTAL REFLECTION

(75) Inventors: Yoshiyuki Kunuki, Kanagawa (JP); Katsuaki Muraishi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 281 days.

(21) Appl. No.: 11/436,487

(22) Filed: May 19, 2006

(65) Prior Publication Data
US 2006/0263874 A1    Nov. 23, 2006

(30) Foreign Application Priority Data
May 19, 2005   (JP)   .............................. 2005-147153

(51) Int. Cl.
*G01N 33/543* (2006.01)
(52) U.S. Cl. ................. 436/518; 435/287.1; 435/287.2; 435/288.7; 435/808; 436/43; 436/524; 436/525; 436/805; 422/63; 422/82.05
(58) Field of Classification Search ....................... None
See application file for complete search history.

(56) References Cited

U.S. PATENT DOCUMENTS

| 5,164,589 | A | 11/1992 | Sjödin |
| 5,313,264 | A | 5/1994 | Ivarsson et al. |
| 5,965,456 | A * | 10/1999 | Malmqvist et al. ........... 436/514 |

FOREIGN PATENT DOCUMENTS

JP    3-294605 A    12/1991

* cited by examiner

*Primary Examiner*—Christopher L Chin
(74) *Attorney, Agent, or Firm*—Sughrue Mion, PLLC

(57) ABSTRACT

A surface plasmon resonance (SPR) assay apparatus has an assay stage, which is loadable with a sensor unit. The sensor unit has a prism, thin film, flow cell and flow channel for flow of sample. A multiple pipette assembly accesses the flow channel in the assay stage, and introduces the sample into the flow channel. A light source applies illuminating light to the thin film to satisfy a total reflection condition. A photo detector receives the illuminating light reflected by the thin film to output a signal. A pressing mechanism presses the sensor unit on the assay stage for holding in a direction of the access of the pipette assembly. The pressing mechanism includes a movable pad for contacting the sensor unit. A slider moves the pad to press the sensor unit. A spring plunger adjusts pressure of the pad to the sensor unit.

16 Claims, 10 Drawing Sheets

APPARATUS AND METHOD OF ASSAY IN UTILIZING ATTENUATED TOTAL REFLECTION

BACKGROUND OF THE INVENTION

1. Field of the Invention

The present invention relates to an apparatus and method of assay in utilizing attenuated total reflection. More particularly, the present invention relates to an apparatus and method of assay in utilizing attenuated total reflection, in which a sensor unit for assay can be positioned reliably to prevent leakage of fluid in use of pipette devices.

2. Description of the Related Art

An assay apparatus for assay in utilizing attenuated total reflection is used for various kinds of studies in a biochemical field or the like, for example to study interaction of protein, DNA and various biomaterials, and to select candidate drugs by screening.

A surface plasmon resonance (SPR) sensor is known as an assay apparatus in utilizing attenuated total reflection. Surface plasmon is a term to mean the compressional wave created on the surface of the metal and included in plasmon as quantized expression of the compressional wave. Free electrons in a metal vibrate to generate the compressional wave.

U.S. Pat. Nos. 5,164,589 and 5,313,264 (corresponding to JP-B 3294605) disclose an SPR assay apparatus in which an optical system of Kretschmann configuration is used for incidence of light to the metal film. According to the Kretschmann configuration, the thin film/dielectric interface of the metal film is fitted on a prism, which condenses light and directs the light to the thin film/dielectric interface in a manner conditioned for total reflection. A sensing surface is overlaid inside the flow channel, for immobilizing the sample. Reaction of the sample is caused on the sensing surface. Illuminating light is applied to the interface of the metal film through the prism to satisfy the total reflection condition, to measure reflected illuminating light.

Upon the total reflection created on the metal/dielectric interface, a small component of the light passes through the metal film without reflection, and penetrates to the sensing surface. A wave of the penetrating component is called an evanescent wave. Surface plasmon resonance (SPR) is created when frequency of the evanescent wave coincides with that of the surface plasmon. In response to this, intensity of the reflected light attenuates remarkably. In the assay apparatus, the attenuation in the reflected light reflected by the metal/dielectric interface is detected, to recognize creation of the SPR on the sensing surface.

A sample or biomaterial, such as protein and DNA, is handled as sample fluid for the purpose of preventing deactivation or modification due to drying. Examples of its content of fluids include pure water, physiological saline water, liquid buffer and the like. The assay apparatus of U.S. Pat. Nos. 5,164,589 and 5,313,264 (corresponding to JP-B 3294605) assays the interaction of the samples. A flow channel is formed at the sensing surface for flow of the sample fluid. The flow channel and the prism are disposed on the assay stage disposed on the apparatus body. A sensor unit of the chip type having the metal film on the support of glass is loaded in the assay stage for assay.

U.S. Pat. Nos. 5,164,589 and 5,313,264 (corresponding to JP-B 3294605) discloses a connector block secured to the flow cell for connecting a tube with the flow channel. However, contamination is likely to occur in the structure with the tube, because a first fluid may be stuck on the inside of the tube and a second fluid will enter and mixes with the residue of the first fluid.

To solve such a problem, it is conceived with an SPR assay apparatus to use a pipette device having a pipette head and a pipette tip fitted on an end of the pipette head in a removable manner. A fluid such as a sample fluid stored in a reservoir is dispensed and introduced to a flow channel inside the assay apparatus. The pipette tip is exchanged at each time the fluid in use is changed over, so contamination of the fluid is prevented in the flow of the fluid to the flow channel.

A sensor unit is used with the assay apparatus, and includes a flow cell, a prism, and a sealing mechanism. The flow cell has the flow channel. A metal film or thin film is overlaid on the prism. The sealing mechanism keeps a lower face of the flow cell fitted on the upper face of the prism, for positioning the metal film in the flow channel. The flow channel is a conduit formed in a U-shape in the flow cell. Ends of the flow channel are open in the upper surface of the flow cell. A lower side of the flow channel is open, and is closed by the metal film. When the fluid is introduced to the flow channel, the fluid contact the metal film positioned in the flow channel. When the fluid is introduced by the pipette device to the flow channel, an end of the pipette device is set at one of the ends of the flow channel, to dispense and introduce the fluid.

However, a problem is likely to arise in incidental offsetting of the sensor unit upon inserting the pipette device in the flow channel or removing the pipette device from the flow channel. As a detection signal of the SPR is very fine, small offsetting of the sensor unit will cause an error in the assay. Also, a direction of removing the pipette device from the flow channel is reverse to a direction of the sealing mechanism pressing the flow cell on the prism. Force of pressing the flow cell will decreased in removal of the pipette device. A gap may occur between the flow cell and the prism, to leak the fluid from the flow channel.

SUMMARY OF THE INVENTION

In view of the foregoing problems an object of the present invention is to provide an apparatus and method of assay in utilizing attenuated total reflection, in which a sensor unit for assay can be positioned reliably to prevent leakage of fluid in use of pipette devices.

In order to achieve the above and other objects and advantages of this invention, an assay apparatus for assay in utilizing attenuated total reflection is provided. There is an assay stage for being removably loaded with a sensor unit including a dielectric medium overlaid with a thin film, and a flow cell having a flow channel for flow of sample in contact with the thin film. A dispenser has a pipette device for accessing the flow channel of the sensor unit set in the assay stage, for dispensing and introducing the sample into the flow channel. A light source applies illuminating light to the thin film to satisfy a total reflection condition. A photo detector receives the illuminating light reflected by the thin film, to convert the illuminating light into an electric output. A pressing mechanism presses the sensor unit on the assay stage for holding in a first direction in which the pipette device is moved for access.

Furthermore, a placing region receives placement of the sensor unit prior to assay with the light source and the photo detector. A sensor shifting mechanism squeezes the sensor unit in the placing region in a second direction being substantially perpendicular to the first direction, and sets the sensor unit in the assay stage.

Furthermore, a clamping mechanism clamps the sensor unit on the assay stage in a third direction being substantially perpendicular to the first direction and to the second direction.

Preferably, the pressing mechanism includes a movable pad having a contact portion for contacting the sensor unit. A moving unit moves the pad to press the sensor unit. A pressure adjuster adjusts pressure of the pad to the sensor unit.

Preferably, the pressure adjuster is constituted by a spring plunger.

Preferably, the contact portion includes a through hole or recess for enabling access of the pipette device to the flow channel while the sensor unit is pressed on the assay stage.

Preferably, the pressing mechanism, prior to holding the sensor unit in a main holding step, presses the sensor unit on the assay stage for at least one time, and shortly discontinues pressing of the sensor unit.

Preferably, the assay stage includes a support for supporting the light source and the photo detector. A rail portion is secured to the support, for receiving a lower surface of the sensor unit, and for keeping the sensor unit slidable while the sensor shifting mechanism shifts the sensor unit. The pressing mechanism contacts an upper surface of the sensor unit for pressing the sensor unit on the rail portion.

Preferably, the sensor unit includes plural sensor cells, arranged in a sensor cell train in the second direction, and respectively having the flow channel and the thin film. The sensor shifting mechanism squeezes the sensor unit in the second direction, and shifts the sensor unit in the second direction, selectively to set the sensor cells in an assay position being within a light path from the light source.

Preferably, the sensor unit has a reference surface being substantially perpendicular to the third direction, and is clamped by the clamping mechanism on the reference surface.

Preferably, the clamping mechanism includes a pin portion stationary on the assay stage. A pressure device is opposed to the pin portion, for pressing the sensor unit on the pin portion.

Preferably, the pressure device is constituted by a spring plunger.

Preferably, the sensor shifting mechanism includes a pickup unit, having first and second holding arms, for squeezing the sensor unit in the second direction between. A moving unit moves the pickup unit in the second direction.

Preferably, the pickup unit includes a first pickup block for supporting the first holding arm. A second pickup block is secured to the first pickup block in a slidable manner, for supporting the second holding arm. A biasing portion biases at least one of the first and second pickup blocks in a direction to come nearer to each other.

Preferably, the moving unit includes a nut portion secured to an outside of the pickup unit. A ball screw is disposed to extend in the second direction, for engagement with the nut portion by helical coupling. A motor rotates the ball screw.

According to one aspect of the invention, an assay method of assay in utilizing attenuated total reflection is provided. An assay stage is removably loaded with a sensor unit including a dielectric medium overlaid with a thin film, and a flow cell having a flow channel for flow of sample in contact with the thin film. The assay stage includes a light source for applying illuminating light to the thin film to satisfy a total reflection condition, and a photo detector for receiving the illuminating light reflected by the thin film, to convert the illuminating light into an electric output. A pipette device is caused to access the flow channel of the sensor unit set in the assay stage, for dispensing and introducing the sample into the flow channel. In the assay method, the sensor unit is pressed on the assay stage for holding in a first direction in which the pipette device is moved for access. While the sensor unit is pressed, the sample is introduced into the flow channel by setting the pipette device, to measure reaction of the sample on the thin film.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

Figure 1A:
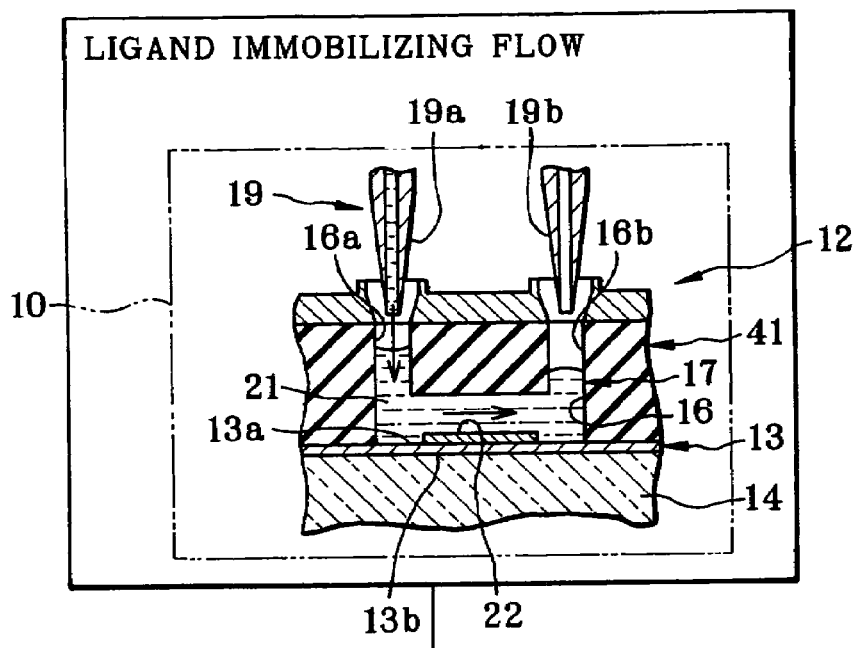
FIG. 1A is an explanatory view in section illustrating a ligand immobilizing flow.
Figure 1B:
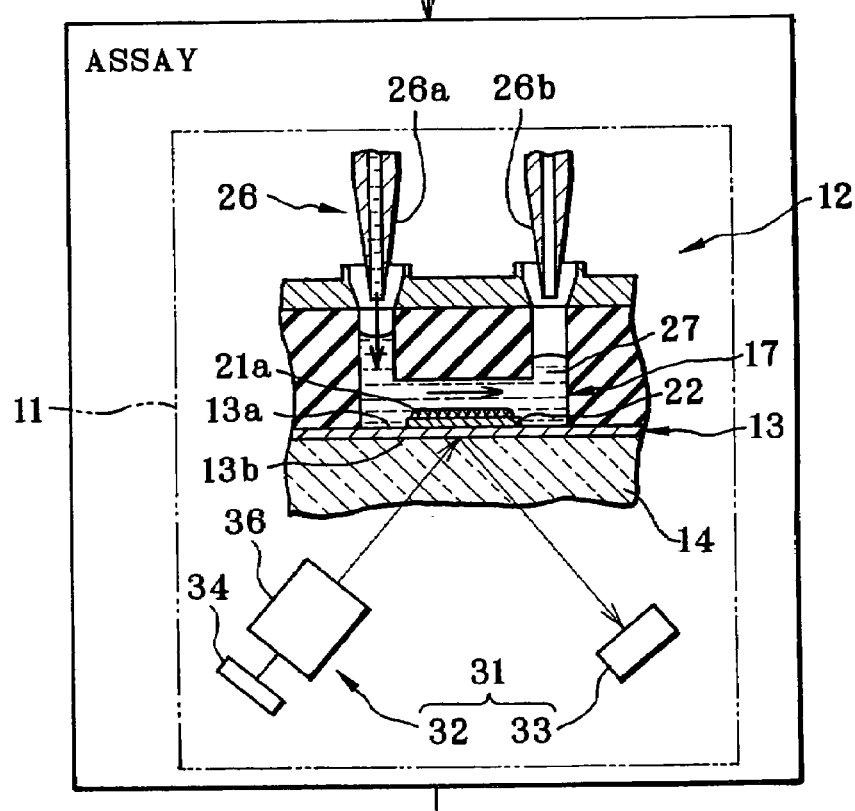
FIG. 1B is an explanatory view in section illustrating an assay and data analysis.

In FIGS. 1A and 1B, a surface plasmon resonance (SPR) assay system is schematically illustrated. The assay system includes a ligand immobilizing apparatus 10, an assay apparatus 11 and a data analyzer. The ligand immobilizing apparatus 10 introduces fluid of ligand toward a sensing surface for the purpose of immobilizing the ligand. The assay apparatus 11 assays interaction between the ligand and an analyte introduced after the ligand immobilization.

The sensor unit 12 includes a thin film 13 of metal, a prism 14 as a dielectric support, and flow cells 41. A first surface of the thin film 13 is a sensing surface 13a where surface plasmon resonance is generated. A second surface of the thin film 13 is an interface 13b defined by connection with the prism 14, and receives light of incidence. A flow channel 16 is formed in the flow cells 41, and causes sample fluids.

An example of material for the thin film 13 is gold (Au) or the like. A thickness of the thin film 13 is 50 nm. The thickness can be changed for the suitability in view of the material of the thin film 13, a wavelength of light to be applied, and the like. The prism 14 is a transparent dielectric block, and overlaid with the thin film 13. Illuminating light is condensed by the prism 14 for application to the interface 13b to satisfy the total reflection condition. The flow channels 16 are in the U shape. Ends of the flow channels 16 respectively include a first orifice 16a and a second orifice 16b. The first orifice 16a receives introduction of a sample fluid. The second orifice 16b is accessed for removing the sample fluid. A horizontal width or diameter of the flow channels 16 is approximately 1 mm. An interval between the first and second orifices 16a and 16b of the flow channel 16 is approximately 10 mm.

A lower side of the flow channels 16 where the flow cell recess is open is enclosed by the prism 14 having the sensing surface 13a. There are defined sensor cells or measuring cells 17 each of which is a portion of the sensing surface 13a closed by the portion about the recess. In the present embodiment, the sensor unit 12 has plural sensor cells 17, for example three. See FIG. 3.

A ligand immobilizing flow is for binding of ligand on the sensing surface 13a. At first, the sensor unit 12 is set in the ligand immobilizing apparatus 10. A multiple pipette assembly 19 is included in the ligand immobilizing apparatus 10, and has a first pipette device 19a and a second pipette device 19b. The first pipette device 19a is set at the first orifice 16a. The second pipette device 19b is set at the second orifice 16b. The first pipette device 19a introduces fluid to the flow channel 16. The second pipette device 19b aspirates and draws fluid from the flow channel 16. The introduction with the first pipette device 19a is at the same time as the removal with the second pipette device 19b. Ligand fluid 21 as sample fluid, as a fluid which contains ligand or biomaterial and fluid medium, is introduced through the first orifice 16a by the multiple pipette assembly 19.

An immobilizing film or linker film 22 is overlaid on the thin film 13 at the center of the sensing surface 13a. The linker film 22 is previously produced in the course of manufacturing the sensor unit 12. As the linker film 22 is a basis for immobilizing the ligand, various materials are available for selective use according to the type of the ligand to be immobilized.

In the ligand immobilizing apparatus 10, pre-treatment before a ligand immobilizing flow with the ligand fluid 21 is wetting of the linker film 22 by use of liquid buffer, and activation of the linker film 22 for the purpose of facilitating binding of the ligand to the linker film 22. An example of an immobilizing method is the amine coupling method. An example of material for the linker film is carboxy methyl dextran, to bind an amino group contained in the ligand with the dextran directly by a covalent bond. An example of liquid for the activation is mixture of N'-(3-dimethylaminopropyl) carbodiimide hydrochloride (EDC) and N-hydroxy imide succinate (NHS). The ligand immobilizing apparatus 10, after the activation, introduces liquid buffer for the ligand immobilizing flow to wash and clean the flow channel 16.

Various liquids are available for use as the liquid buffer for the ligand immobilizing flow, and solvent or diluent for the ligand fluid 21. Examples of the liquids include buffer liquids, or physiological saline water and other aqueous solutions of physiological salts, and pure water. It is possible according to a type of the ligand to determine suitably solution types and pH values of the solutions, and types of substances to be mixed, and their density. If a biomaterial is used as a ligand, physiological saline water is used of which pH value is kept neutralized. In the amine coupling method described above, the linker film 22 is electrified negatively because of the carboxy methyl dextran. In consideration of this, it is possible to use phosphatic buffered saline (PBS) solution having strong operation of buffer and containing phosphate salt at high density which is not physiological, because protein can be electrified positively for the purpose of facilitating binding with the linker film 22.

The ligand immobilizing apparatus 10, after the activation and washing, introduces the ligand fluid 21 to the flow channel 16 for immobilization. Ligand 21a as sample such as biomaterial diffused in the ligand fluid 21, in introduction to the flow channel 16, gradually migrates to and binds with the linker film 22. This is the ligand immobilizing flow of the ligand 21a on the sensing surface 13a. It is general that a step of the immobilization requires approximately one (1) hour, during which the sensor unit 12 is preserved in an environment conditioned suitably, for example at a conditioned temperature. Until the immobilization, the ligand fluid 21 in the flow channel 16 may be left to stand in a stationary state. However, the ligand fluid 21 can be preferably stirred or turbulently flowed for ensured fluidity in the flow channel 16. The stirring or turbulent flow can promote binding of the ligand 21a with the linker film 22, to raise an immobilized amount of the ligand 21a.

When the immobilization of the ligand 21a on the sensing surface 13a is completed, the ligand immobilizing apparatus 10 removes the ligand fluid 21 from the flow channel 16. Namely, the second pipette device 19b draws the ligand fluid 21 by aspiration. After this, the sensing surface 13a is washed by introducing washing liquid into the flow channel 16. In the ligand immobilizing apparatus 10, a blocking step is made after the washing. A blocking liquid is introduced into the flow channel 16, to deactivate the reaction group remaining without binding with the ligand. A preferable example of the blocking liquid is ethanol amine hydrochloride. After the blocking, the flow channel 16 is washed again. The ligand immobilizing apparatus 10 introduces evaporation retardant to the flow channel 16 after the final washing. The sensor unit 12 is left to stand until the assay, with the sensing surface 13a humid on the evaporation retardant.

For the assay, the sensor unit 12 is set in the assay apparatus 11. A multiple pipette assembly 26 as fluid dispenser is installed in the assay apparatus 11, and structurally the same as the multiple pipette assembly 19 in the sample immobilizing device 10. The multiple pipette assembly 26 introduces fluid to the flow channel 16 through the first orifice 16a. For the assay in the assay apparatus 11, at first, liquid buffer is introduced into the flow channel 16, and caused to flow continuously for a prescribed time. After this, analyte solution or analyte fluid 27, as a fluid which contains analyte and fluid medium that may be solvent, is introduced into the flow channel 16. Then liquid buffer is introduced again. Note that the flow channel 16 may be cleaned or washed before initially introducing the liquid buffer. Reading of data in a photo detector starts upon initially introducing the liquid buffer in order to detect a reference level of a signal. The reading is continued until the introduction of the liquid buffer at the second time after entry of analyte fluid 27. It is possible not only to detect the reference level that is a base line, but to assay interaction or reaction between the analyte and the ligand, and to measure a signal until dissociation between the analyte and ligand in response to introduction of the liquid buffer.

Various liquids are available for use as the liquid buffer for assay, and solvent or diluent for the analyte fluid 27. Examples of the liquids include buffer liquids, or physiological saline water and other aqueous solutions of physiological salts, and pure water. It is possible according to a type of a ligand or analyte to determine suitably solution types and pH values of the solutions, and types of substances to be mixed, and their density. To facilitate dissolving of the analyte, dimethyl sulfo-oxide(DMSO) can be added to the physiological saline water. The use of the DMSO considerably influences to a level of an output signal. The buffer for assay is used for detecting the reference level of the signal, as described above. If DMSO is contained in the fluid for the analyte, it is preferable to use buffer for assay at a DMSO density approximately equal to that of the fluid in the analyte.

In general, the analyte fluid 27 may be kept preserved for a long time, for example one (1) year. It is likely that a difference occurs between an initial level and a current level of the DMSO density owing to a change with time. If assay with high precision is required, such a difference in the density is estimated according to the reference signal (ref-signal) level upon introducing the analyte fluid 27, so that measured data can be compensated for by DMSO density compensation.

The reference signal or ref-signal is an output of the SPR derived from the reference region on the sensing surface and free from immobilization of a ligand, and is a basis of comparison with a measuring signal. The measuring signal or act-signal is an output of the SPR derived from the measuring region on the sensing surface and for immobilization of a ligand to react with an analyte. The data analyzer effects data analysis by obtaining a difference or ratio of the act-signal and ref-signal output by the assay apparatus. For example, the data analyzer obtains data of a finite difference between the act-signal and ref-signal, and analyzes various items according to the finite difference. This makes it possible to cancel electric noise caused by external irregularities, such as individual specificity of the sensor unit or the linker film, mechanical changes of the assay apparatus, temperature changes of the liquid, and the like. A signal with a high S/N ratio can be obtained.

Compensation data for the DMSO density compensation is obtained before introducing the analyte fluid 27. A plurality of liquid buffers different in the DMSO density are introduced to the sensor cells 17. Amounts of changes in the levels of ref-signal and act-signal are evaluated so as to obtain the compensation data.

An optical assay unit 31 is constituted by the illuminator 32 and a photo detector 33. The reaction between the ligand and analyte can be recognized as a change of a resonance angle, which is an angle of incidence of light received by the interface 13b. To this end, the illuminator 32 is caused to apply light to the interface 13b at various values of angles of incidence satisfying a condition of the total reflection. The illuminator 32 includes a light source 34 and an optical system 36, which includes a condensing lens, a diffusing plate and a polarizer. Their position and angle of installation are so determined that an angle of incidence of the light satisfies the condition of the above total reflection.

Examples of the light source 34 include a light emitting diode (LED), laser diode (LD), super luminescent diode (SLD), and other light emitting element. A single element is used as the light source 34 as a point light source, to illuminate the interface 13b in a sensor cell. Note that, if simultaneous assay of plural sensor cells is desired, light from a single light source may be separated into plural light paths for application to the sensor cells. Alternatively, a plurality of light sources may be arranged for association with respectively the sensor cells.

The diffusing plate diffuses light from the light source 34, and suppresses onset of irregularity in the light amount. The polarizer allows only p-polarized light to pass, the p-polarized light creating the surface plasmon resonance. Note that no polarizer is required if directions of rays emitted by the light source 34, for example an LD, are kept equal. However, a diffusing plate may be combined with the light source 34 of a type of which directions of emitted rays are kept equal. Directions of rays in polarization are changed to an unequal state by the passage through the diffusing plate. For this structure, the polarizer can be utilized to set equal the directions of the rays. The light obtained after the diffusion and polarization is condensed by a condensing lens, and directed to the prism 14. It is possible to travel rays with various angles of incidence toward the interface 13b without irregularity in the intensity.

The photo detector 33 receives light reflected by the interface 13b of the thin film 13, and detects intensity of the light. Rays of light are incident upon the interface 13b at various angles. The light is reflected by the interface 13b at various angles of reflection according to the angles of the incidence. The photo detector 33 receives the light at various angles of the reflection. When a medium in contact with the sensing surface 13a changes, the refractive index also changes. The angle of incidence of light with attenuation of reflected light is changed. When the analyte fluid is introduced to the sensing surface 13a, a resonance angle changes according to interaction between the analyte and the ligand.

An example of the photo detector 33 is a CCD area sensor or an array of photo diodes, which receives light reflected by the interface 13b at various angles of reflection, and photoelectrically converts the light into an output of SPR. The interaction between the ligand and analyte is recognized as information of shifting of a position of attenuation of the reflected light on the photo reception surface of the photo detector 33. A refractive index of the thin film with the sensing surface 13a of the linker film becomes different between the states before and after the contact of the ligand with the analyte. Thus the resonance angle at which surface plasmon resonance occurs changes between those states. When reaction starts by the contact between the analyte and ligand, the resonance angle starts changes, to start shifting the attenuation position of the reflected light on the photo reception surface. The photo detector 33 outputs and sends an SPR signal to the data analyzer. The data analyzer analyzes the SPR output from the assay apparatus 11, to recognize interaction between the analyte and ligand.

Figure 2:
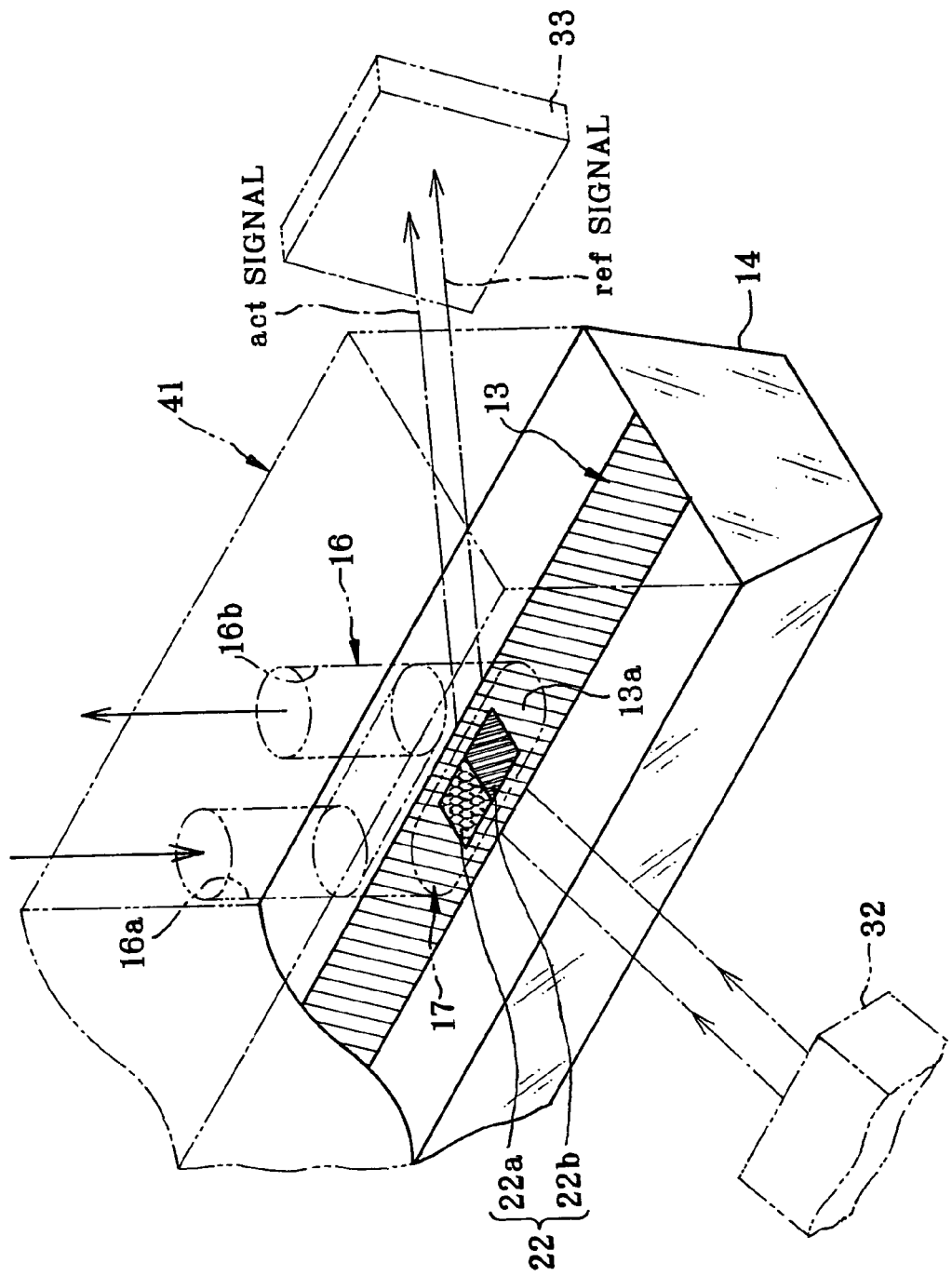
FIG. 2 is a perspective view illustrating a sensor cell.

Note that in FIG. 2, the illuminator 32 and the photo detector 33 in the optical assay unit 31 are positioned so that a direction of light projected and reflected between those intersects horizontally with a flow of the flow channel 16, which is unlike the structure depicted in FIG. 1B. The state of FIG. 1B is simplified for the convenience. However, in the invention the illuminator 32 and the photo detector 33 may be positioned according to in FIG. 1B so that a direction of light projected and reflected between those is horizontally aligned with the flow of the flow channel 16 between the pipettes.

In FIG. 2 with the linker film 22, there are a measuring region 22a (act) and a reference region 22b (ref) formed in the linker film 22. The measuring region 22a has immobilization of a ligand, and is a region for reaction between the ligand and analyte. The reference region 22b does not have immobilization of a ligand, and is used for outputting a reference signal for comparison with a signal retrieved from the measuring region 22a. Note that the reference region 22b is formed in the course of film production of the linker film. An example of a process of the forming has steps of surface processing of the linker film 22 at first, and then deactivating the reaction groups in approximately a half of an entire area of the linker film 22 for binding with ligand. Thus, a half of the linker film 22 becomes the measuring region 22a. A remaining half of the linker film 22 becomes the reference region 22b.

The photo detector 33 outputs an act-signal for the measuring region 22a, and a ref-signal for the reference region 22b. The act-signal and ref-signal are simultaneously measured in a period between the detection of the reference level, association and dissociation. The data analyzer effects data analysis by obtaining a difference or ratio of the act-signal and ref-signal output by the assay apparatus 11. For example, the data analyzer obtains data of a finite difference between the act-signal and ref-signal, and analyzes various items according to the finite difference. This makes it possible to cancel electric noise caused by external irregularities, such as individual specificity of the sensor unit 12 or the linker film 22, mechanical changes of the assay apparatus 11, temperature changes of the liquid, and the like. A signal with a high S/N ratio can be obtained.

The illuminator 32 and the photo detector 33 are constructed for measurement of two signal channels of the act-signal and ref-signal. To this end, a mirror for reflection is associated with the illuminator 32, for separating light from a single light-emitting element into plural light paths which are directed to the measuring and reference regions 22a and 22b. The photo detector 33 is constructed by photo diode arrays each of which is associated with one of the two signal channels, and receives the light on the light paths.

If a CCD area sensor is used as the photo detector 33, reflected light of the dual channels received at the same time can be recognized as an act-signal and ref-signal by the image processing. However, such a method according to the image processing might be too difficult. Alternatively, signals of the signal channels can be received by differentiating the time sequence for a very small period of time of the incidence between the measuring and reference regions 22a and 22b. An example of differentiating the time sequence is a use of a disk disposed on a light path and having two holes positioned at 180 degrees of a rotational angle. The disk is rotated to shift the time sequence between the signal channels. The holes are disposed at a difference of the radius from the rotational center in association with the interval between the measuring and reference regions 22a and 22b. When a first one of the holes enters the light path, illuminating light travels to the measuring region 22a. When a second one of the holes enters the light path, the light travels to the reference region 22b.

Figure 3:
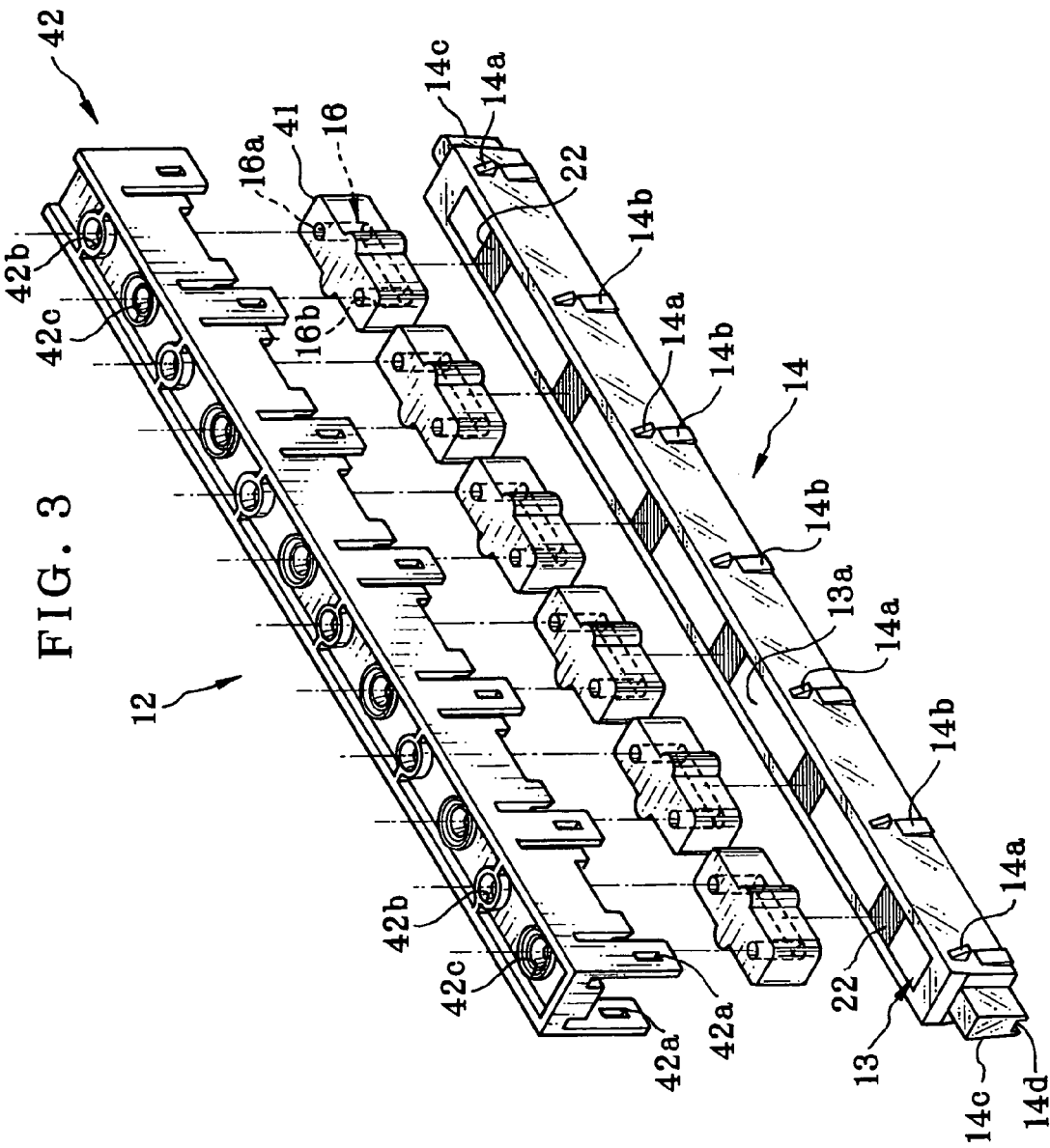
FIG. 3 is an exploded perspective illustrating a sensor unit.

In FIG. 3, the sensor unit 12 is illustrated structurally. The sensor unit 12 includes the flow cells 41, the prism 14, and a sealing mechanism 42. The prism 14 is dielectric, and is overlaid with the thin film 13 on its upper surface. The sealing mechanism 42 keeps the flow cells 41 positioned by fitting its lower surface on the upper surface of the prism 14. Six regions of the linker film 22 are defined on the surface of the thin film 13 for immobilizing ligand. Those regions are arranged in the longitudinal direction of the prism 14 and the thin film 13 at a predetermined interval. The flow cells 41 are associated with respectively the regions of the linker film 22, and arranged on the thin film 13 to position the flow channel 16 on the linker film 22. Note that, in the sensor unit 12, the number of the linker film 22 or the flow cells 41 may not be six, but can be five or less, or seven or more. Also, a single flow cell of a great length may be used in the invention, and can have six flow channel 16 arranged in a channel array.

The flow cells 41 are formed nearly in a box shape. The flow channel 16 extends in a U shape in the longitudinal direction of the flow cells 41. The flow channels 16 constitute the sensor cells 17 together with the thin film 13 in connection with its lower surface. See FIGS. 1A and 1B. Thee flow cells 41 are formed from elastic material for the purpose of ensuring tightness in contact with the thin film 13. Examples of elastic materials include rubber, polydimethylsiloxane (PDMS), and the like. When the lower surface of the flow cells 41 is pressed on an upper surface of the prism 14, the flow cells 41 are elastically deformed, to remove a space between its surface and the thin film 13. Open lower portions of the flow channels 16 are closed fluid-tightly by the upper surface of the prism 14.

The thin film 13 is formed by vapor deposition on the prism 14. Retention claws 14a are formed to project from the prism 14 at its sides as viewed longitudinally. Retention portions 42a of the sealing mechanism 42 are engageable with the retention claws 14a. The flow cells 41 are sandwiched between the sealing mechanism 42 and the prism 14. A lower surface of the flow cells 41 is kept fitted on the prism 14. An erect reference surface 14b is formed on the outside of the prism 14 and under the retention claws 14a. For the purpose of condensing light toward the thin film 13, the prism 14 is so formed that a width of an upper face with the thin film 13 is greater than a width of a lower face. Lateral surfaces of the prism 14 extending in the longitudinal direction are oriented with an inclination with respect to the vertical direction. In contrast, the erect surface 14b extends in the vertical direction. The erect surface 14b is used during holding of the sensor unit 12.

Engageable projections 14c protrude from ends of the prism 14 as viewed in its longitudinal direction. A sensor holder 45 of FIG. 4 contains a plurality of sensor units 12 and loaded in the ligand immobilizing apparatus 10 or the assay apparatus 11. The engageable projections 14c are formed for positioning the sensor unit 12 in a contained state by engagement with the sensor holder 45. Also, a recess 14d is formed in a lower surface of the prism 14 and extends in its longitudinal direction. The recess 14d is used for transfer of the sensor unit 12 in the assay apparatus 11 in the assay step.

Various materials can be used for forming the prism 14, their examples including optical glasses, such as borosilicate crown (BK7) glass, barium crown (Bak4) glass, and the like; and optical plastic materials, such as polymethyl methacrylate (PMMA), polycarbonate (PC), amorphous polyolefin (APO) and the like.

First and second apertures 42b and 42c are formed in the sealing mechanism 42, and positioned at each of the first and second orifices 16a and 16b of the flow channel 16, for entry of an end of each of the first and second pipette devices 19a and 19b, and pipette devices 26a and 26b. The first and second apertures 42b and 42c have a funnel shape with a decreasing diameter for introducing liquid ejected by the pipette toward the first orifice 16a. A lower face of the first and second apertures 42b and 42c is connectable with the first and second orifices 16a and 16b of the flow channel 16 for flow of fluid with the sealing mechanism 42.

Note that an RFID tag (radio frequency identification tag) as a non-contact IC memory may be used with and secured to any one of elements in the sensor unit 12 such as the prism 14 and the sealing mechanism 42. An ID number for the sensor unit 12 is stored in the RFID tag of the read only type. The ID number is read out at each time before operation of one of sequential processes, so the sensor unit 12 can be identified. It is possible to prevent failure or errors in simultaneous immobilization and assay of plural sensor units, such as erroneous introduction of analyte fluid, misreading of results of measurement. Also, the RFID tag may be a writeable type. Information can be written to the RFID tag in sequential processes, such as types of immobilized ligand, date of immobilization, types of analytes used in the reaction, and the like.

Figure 4:
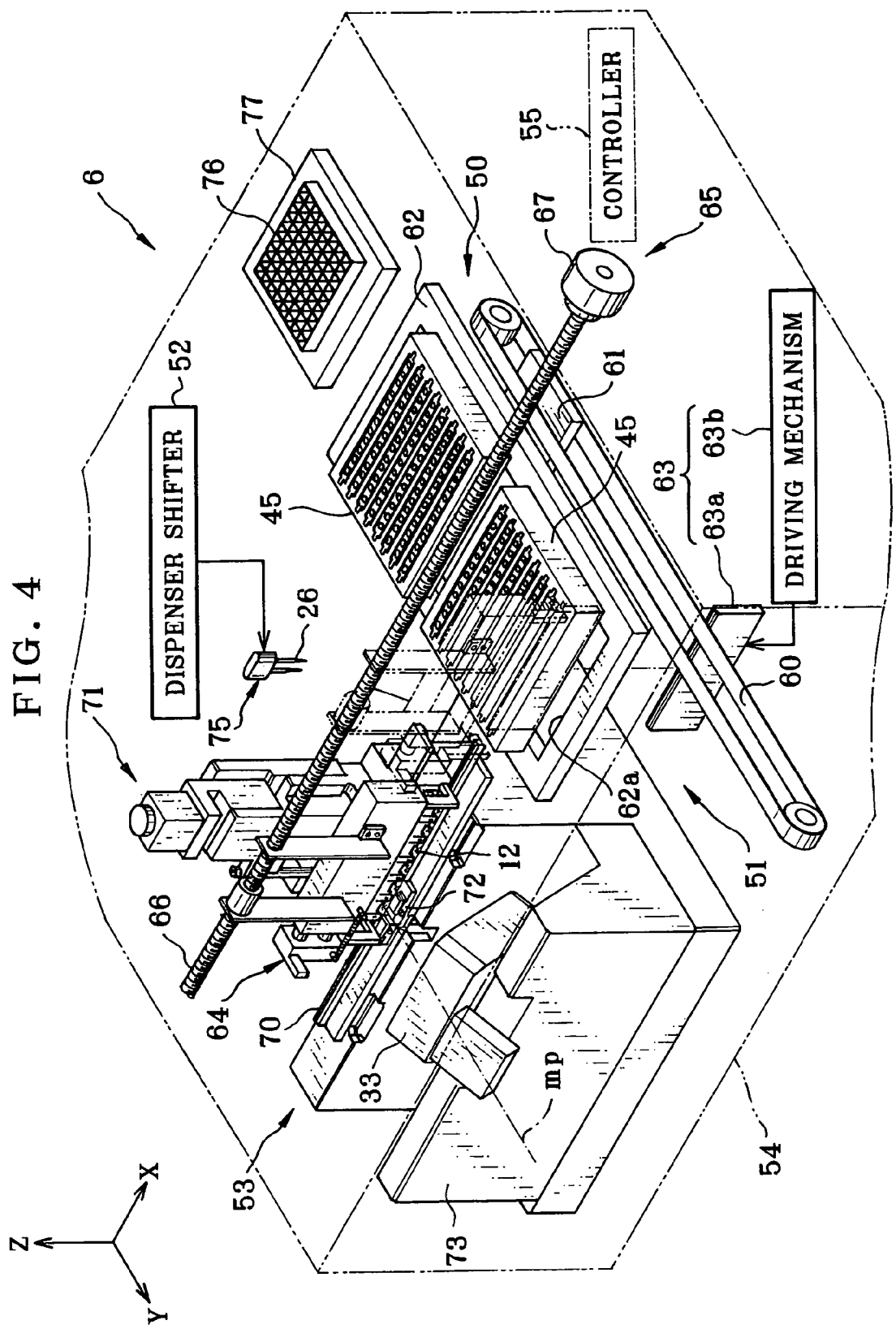
FIG. 4 is a perspective view illustrating an assay apparatus.

In FIG. 4, the assay apparatus 11 is illustrated schematically. The assay apparatus 11 includes a holder moving mechanism 50, a sensor shifting mechanism 51, a dispenser shifter 52 or pipette head shifting mechanism, and an assay stage 53. A casing 54 contains those included in the assay apparatus 11. A controller 55 controls the elements of the assay apparatus 11 in an entire manner. The holder moving mechanism 50 includes a belt 60, a carriage 61, and a placing region 62 with a plate. The carriage 61 is secured to the belt

60. The placing region 62 is disposed on the carriage 61, and supports the sensor holder 45 containing the sensor unit 12 after the ligand immobilizing flow. The holder moving mechanism 50 shifts the placing region 62 with the sensor holder 45 in the direction Y, and moves the sensor unit 12 in the sensor holder 45 to the ready position of the sensor shifting mechanism 51 for pickup.

The sensor holder 45 contains a plurality of the sensor units 12, for example eight. A slit or cutout is formed in the sensor holder 45 for positioning the sensor unit 12 by engagement with the engageable projections 14c. A lower panel of the sensor holder 45 has an opening formed in a portion different from portions to support ends of the sensor unit 12. The placing region 62 has a frame shape for placing the sensor holder 45. An opening 62a is defined in the placing region 62 and associated with the opening in the sensor holder 45.

The sensor shifting mechanism 51 picks up the sensor unit 12 from the sensor holder 45, and includes a first sensor shifter 63, a handling head or pickup unit 64, and a handling head driving unit 65 or X axis moving unit in a second sensor shifter. The first sensor shifter 63 shifts up the sensor unit 12 from the sensor holder 45. The pickup unit 64 squeezes and holds the sensor unit 12 shifted up by the first sensor shifter 63 over the sensor holder 45. The handling head driving unit 65 shifts the pickup unit 64 in the X direction. The first sensor shifter 63 includes a shifting panel 63a and a driving mechanism 63b. The shifting panel 63a moves up through the opening 62a in the placing region 62, and contacts the lower face of the sensor unit 12 in the opening of the sensor holder 45 to shift up the sensor unit 12. The shifting panel 63a is movable in the Z direction. A ready position described above is opposed to the shifting panel 63a.

Figure 5:
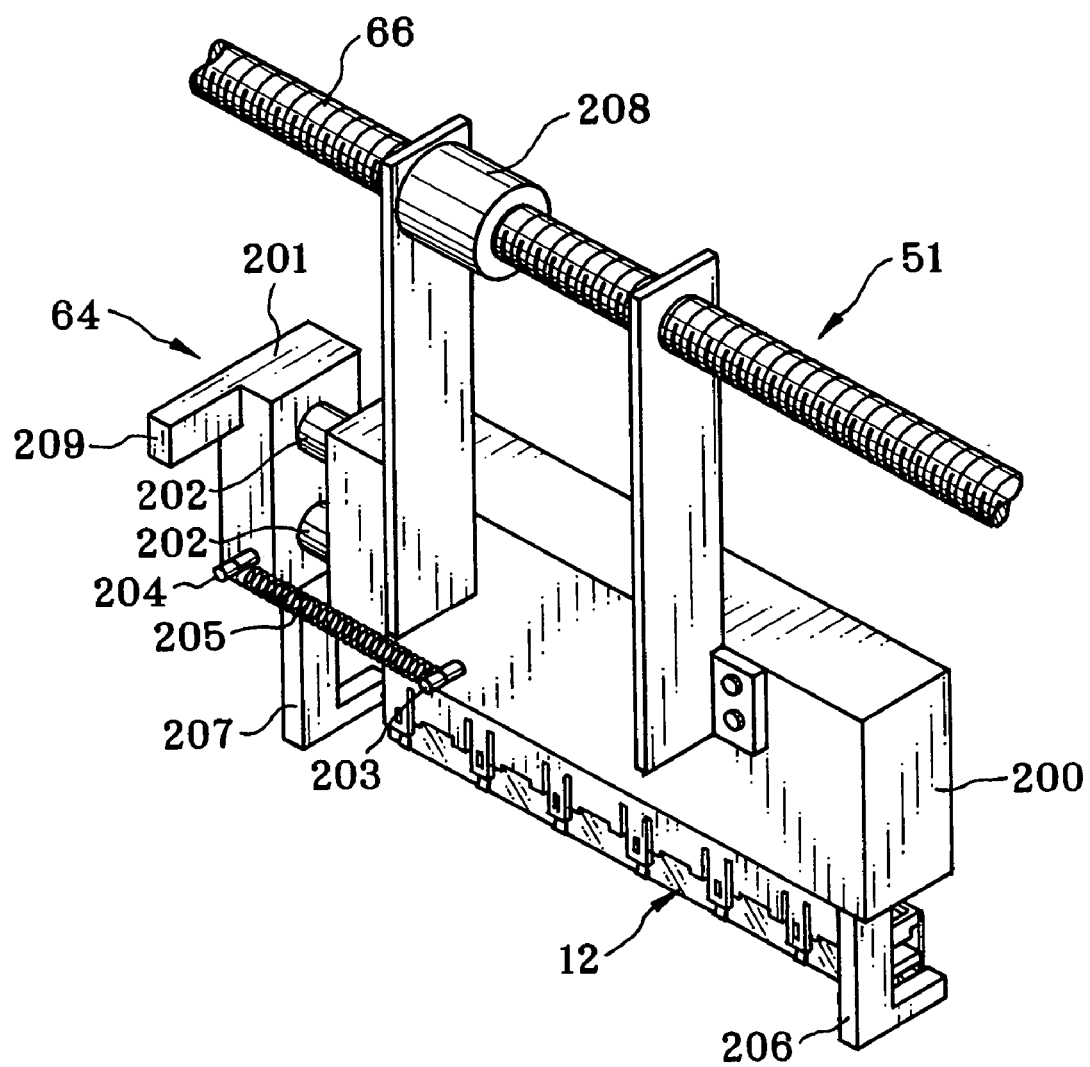
FIG. 5 is a perspective view illustrating a handling head or pickup unit.

In FIG. 5, a structure of the handling head or pickup unit 64 is illustrated in enlargement. The pickup unit 64 includes a first pickup block 200 or head body, and a second pickup block or movable board 201. Two rods 202 connect the movable board 201 with the first pickup block 200. Slide bearings or other bearings of a rectilinear type (not shown) are formed with the first pickup block 200. The rods 202 are inserted in the bearings to keep the movable board 201 slidable in the X direction on the first pickup block 200. Pins 203 and 204 are disposed to project from the first pickup block 200 and the movable board 201. A tension coil spring 205 is connected between the pins 203 and 204 to move the movable board 201 toward the first pickup block 200. L-shaped holding arms 206 and 207 are formed to project from respectively the first pickup block 200 and the movable board 201. In FIGS. 4 and 5, the holding arms 206 and 207 of the pickup unit 64 squeeze the sensor unit 12. When the pickup unit 64 does not squeeze, the tension coil spring 205 exerts force to keep the movable board 201 in contact with the first pickup block 200. See FIG. 6A. An interval between the holding arms 206 and 207 is slightly smaller than a length of the sensor unit 12 in contact between the first pickup block 200 and the movable board 201.

A nut portion 208 is disposed on the first pickup block 200. In FIG. 4, the handling head driving unit 65 or X axis moving unit includes a ball screw 66 and a stepping motor 67 for rotating the ball screw 66. The nut portion 208 is coupled with the handling head driving unit 65. The stepping motor 67 is connected with the controller 55, and causes the ball screw 66 to rotate stepwise at one regular angle in response to a pulse form the controller 55. The ball screw 66 in connection with the nut portion 208 moves the handling head or pickup unit 64 in the X direction according to rotational angle of the stepping motor 67 and a helical pitch. Thus, the pickup unit 64 moves between the pickup position and the assay position mp of the assay stage 53. The pickup unit 64 squeezes the sensor unit 12 in the pickup position, shifts in the X direction to transfer the sensor unit 12 to the assay position mp. After the assay, the pickup unit 64 shifts to the pickup position for releasing the sensor unit 12, which is returned to the sensor holder 45 after the assay.

Figure 6:
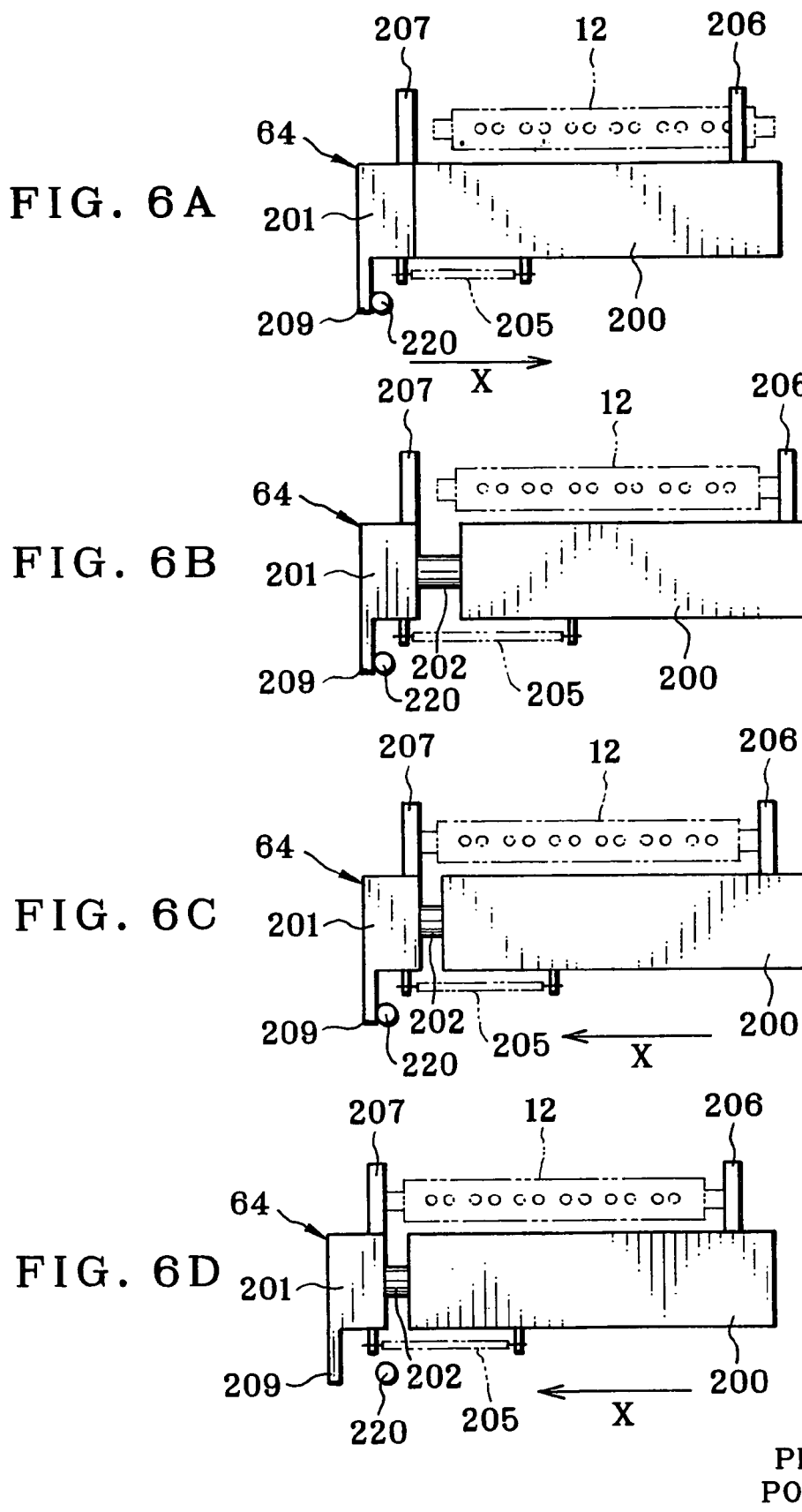
FIG. 6A is an explanatory view in plan illustrating an initial step for pickup of a sensor unit.
FIG. 6B is an explanatory view in plan illustrating a state in which the handling head becomes open.
FIG. 6C is an explanatory view in plan illustrating a state of halfway shutting of the handling head.
FIG. 6D is an explanatory view in plan illustrating a state of completion of the pickup of the sensor unit.

To squeeze the sensor unit 12 with the handling head or pickup unit 64, the first sensor shifter 63 shifts to the pickup position in a state of not raising the sensor unit 12. A contact projection 209 is formed on the second pickup block or movable board 201 in a panel shape. In FIG. 6A, a stopper pin 220 comes to contact the contact projection 209 when the pickup unit 64 moves to the pickup position. The pin 220 is fixedly secured, for example, on the casing 54 of the assay apparatus 11, and stops the movable board 201 from further moving in contact with the contact projection 209.

In FIG. 6B, the first pickup block 200 pulls the second pickup block or movable board 201 against the bias of the tension coil spring 205, to shift to the pickup position, the movable board 201 being retained by the pin 220. An interval between the holding arms 206 and 207 increases. The handling head or pickup unit 64 becomes ready to receive the sensor unit 12. In the first sensor shifter 63, the driving mechanism 63b is driven upon the reach of the pickup unit 64 to the pickup position. The driving mechanism 63b shifts up the sensor unit 12 in the sensor holder 45 to a level where the holding arms 206 and 207 in the pickup unit 64 can squeeze. The pickup unit 64 starts shifting toward the assay position mp in response to the rise of the sensor unit 12 by the first sensor shifter 63.

In FIG. 6C, the sensor unit 12 is squeezed by the holding arms 206 and 207 of which an interval is reduced in the course of shift toward the assay position mp. An interval between the holding arms 206 and 207 is slightly smaller than a length of the sensor unit 12 during the contact of the first pickup block 200 and the second pickup block or movable board 201. The holding arm 207 of the movable board 201 contacts the sensor unit 12 in a position drawn out by the amount of being narrowed, and keeps the sensor unit 12 fixed together with the holding arm 206 of the first pickup block 200 according to the bias of the tension coil spring 205. In FIG. 6D, the handling head or pickup unit 64 with the sensor unit 12 shifts toward the assay position mp, and sets the sensor unit 12 in the assay position mp. Note that, if return of the sensor unit 12 to the sensor holder 45 is desired, a process reverse to that described above can be effected.

In FIG. 4, the assay stage 53 includes the illuminator 32 (See FIG. 9), the photo detector 33, a rail portion 70, a Z axis pressing mechanism 71 for a first direction, a Y axis clamping mechanism 72 for a third direction, and a support 73. The illuminator 32 and the photo detector 33 cooperate for assay with the sensor unit 12. The rail portion 70 guides movement of the sensor unit 12. The Z axis pressing mechanism 71 presses the sensor unit 12 in the assay position mp on the rail portion 70 for retention in the Z direction. The Y axis clamping mechanism 72 clamps the sensor unit 12 at its lateral faces for retention in the Y direction. The support 73 supports those elements.

A rail ridge 68 is formed on the rail portion 70 for engagement with the recess 14d of the sensor unit 12. A rail ridge 68 is also formed on a top end of the shifting panel 63a to contact the sensor unit 12 and in a manner similar to the rail portion 70 for engagement with the recess 14d. The driving mechanism 63b shifts up the shifting panel 63a so that the face of the shifting panel 63a having the rail ridge 68 becomes flush with the rail portion 70. The handling head or pickup unit 64 squeezes the sensor unit 12 in the pickup position, and shifts the sensor unit 12 between the pickup position and assay position mp in smooth contact with the rail portion 70. The sensor unit 12 can be prevented from dropping in the course of movement, and can be handled and shifted between plural positions.

The illuminator 32 and the photo detector 33 are so disposed that the rail portion 70 lies between those. The sensor unit 12 has six sensor cells 17, each of which operates for the assay. The controller 55 sends pulses to the stepping motor 67 to shift the sensor unit 12 by the pitch of arrangement of the sensor cells 17. The sensor cells 17 are set in the assay position mp which is defined within a light path of the illuminator 32.

Figure 7:
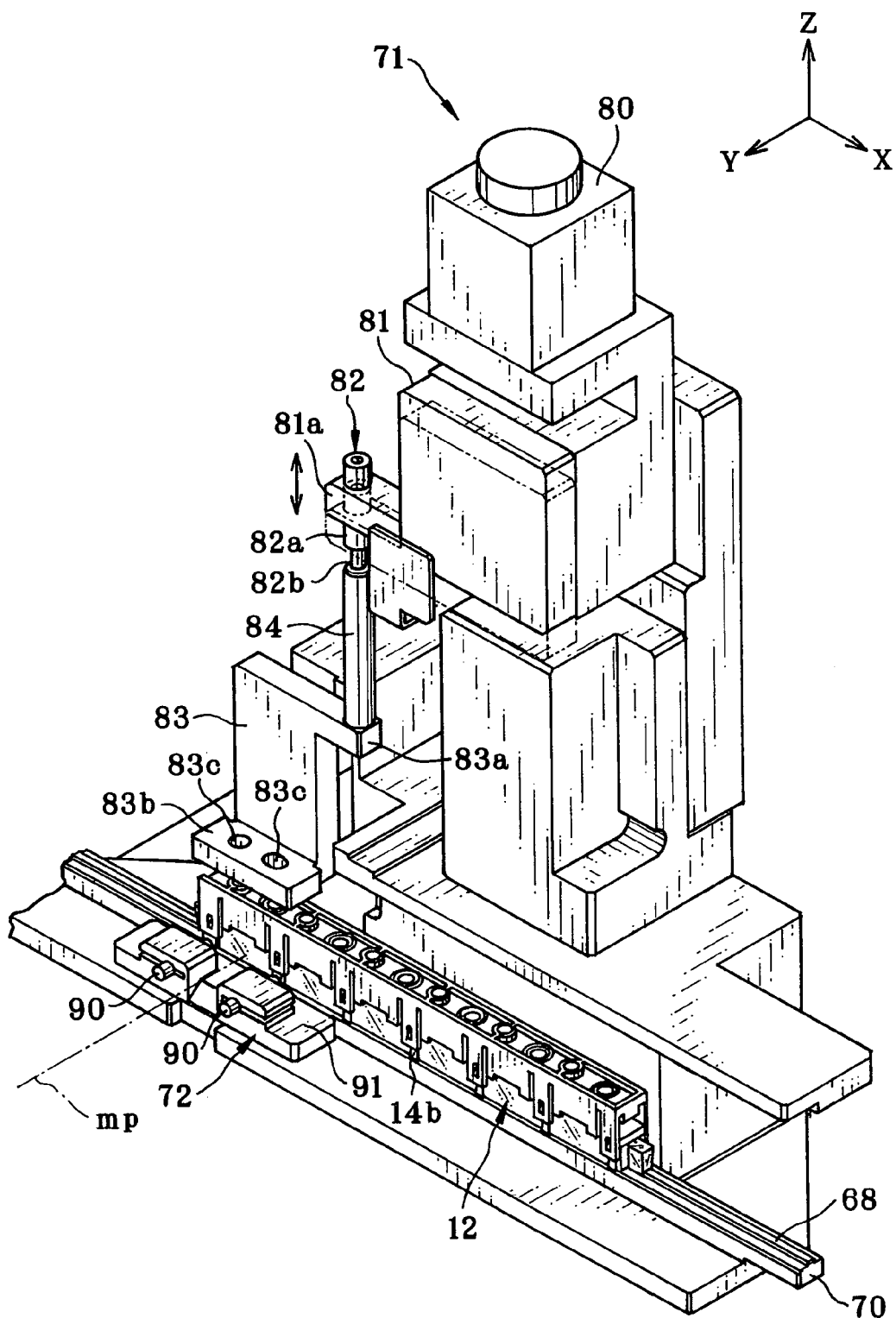
FIG. 7 is a perspective view illustrating a Z axis pressing mechanism.

In FIG. 7, the Z axis pressing mechanism 71 is illustrated. The Z axis pressing mechanism 71 includes a stepping motor 80, a slider 81, a pressure adjusting spring plunger 82 or other suitable plunger mechanism, and a panel shaped movable pad 83 for pressing. The stepping motor 80 is connected with the controller 55 of the assay apparatus 11, and driven to rotate according to pulses from the controller 55. A sliding mechanism, in a form of rack and pinion, connects the stepping motor 80 with the slider 81, and converts rotational shift to linear movement. The slider 81 is slid by rotations of the stepping motor 80 between a first position and a second position, and when in the first position of the phantom line, presses the sensor unit 12 against the rail portion 70, and when in the second position of the solid line, releases the sensor unit 12 from pressure. An arm 81a is formed together with the slider 81 in a panel form. The spring plunger 82 is firmly secured to the arm 81a.

The spring plunger 82 includes a cylindrical case or plunger receptacle 82a and a plunger head 82b. A compression coil spring (not shown) is contained in the plunger receptacle 82a, and biases the plunger head 82b in a direction to the outside. The plunger head 82b shifts to the inside of the plunger receptacle 82a with compression in response to pressure. The plunger head 82b, when released from the pressure, comes to protrude from the plunger receptacle 82a in response to biasing.

An arm 83a is a portion of the panel shaped movable pad 83. A rod shaped connector 84 is firmly secured to the arm 83a. The movable pad 83 in the L shape is secured to the plunger head 82b of the spring plunger 82 by the arm 83a and the rod shaped connector 84. As the spring plunger 82 is secured to the slider 81, the spring plunger 82, the movable pad 83 and the rod shaped connector 84 are shifted in the Z direction together with the slider 81. Sizes of the movable pad 83 and the rod shaped connector 84 are predetermined so that, when the slider 81 is set in the holding position, a lower face of the movable pad 83 is positioned lower than the upper face of the sensor unit 12. This is indicated by the phantom line in FIG. 8A.

Figure 8A:
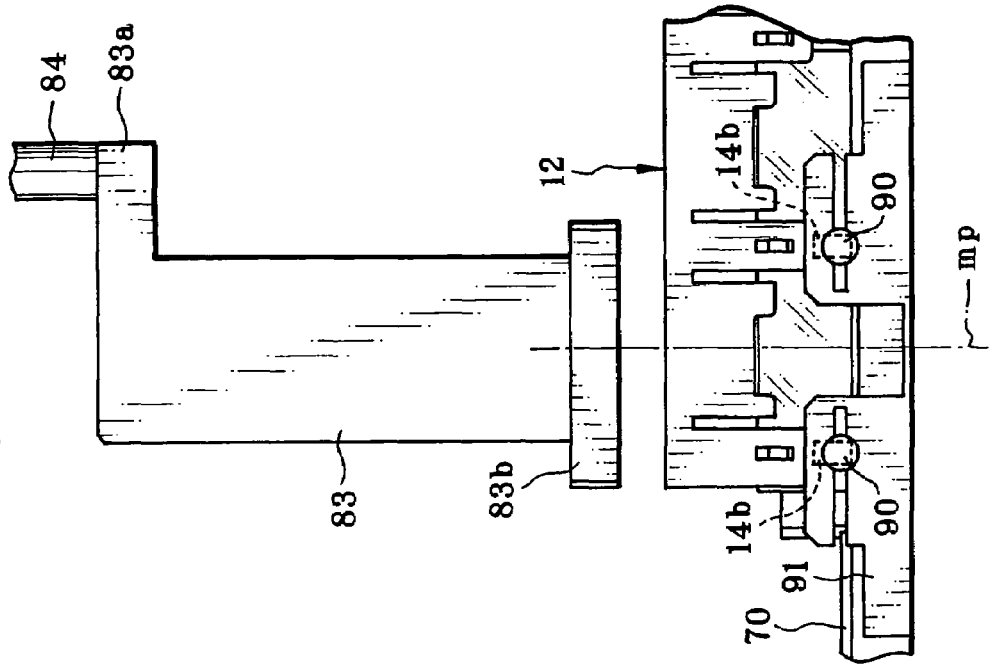
FIG. 8A is an explanatory view in elevation illustrating a panel shaped movable pad with the sensor unit.

When the sensor unit 12 is in the assay position mp, the lower face of the panel shaped movable pad 83 contacts an upper face of the sensor unit 12 as indicated by the solid line of FIG. 8A. As the movable pad 83 shifts lower than the upper face of the sensor unit 12, a difference A from an originally intended position occurs. The plunger head 82b of the spring plunger 82 is pressed and retracted inside the plunger receptacle 82a by an amount equal to the difference A for compensation. The plunger head 82b is biased in a direction to protrude from the plunger receptacle 82a, and transmits the force of the spring to the movable pad 83 by means of the rod shaped connector 84. The movable pad 83 in contact with the sensor unit 12 presses the sensor unit 12 against the rail portion 70 according to the bias of the spring plunger 82.

A contact portion 83b in the L shape has a width corresponding to a region of one of the sensor cells 17 of the sensor unit 12. The panel shaped movable pad 83 presses the sensor cells 17 as target in the assay position mp and keeps the sensor unit 12 in the assay position mp even in access or removal of the multiple pipette assembly 26. In FIG. 5, a through hole 83c is formed in the contact portion 83b for access of the multiple pipette assembly 26 to the sensor cells 17 while the sensor unit 12 is held. Note that a cutout, recess, notch or other shape may be formed in place of the through hole 83c for the purpose of access of the multiple pipette assembly 26.

Figure 8B:
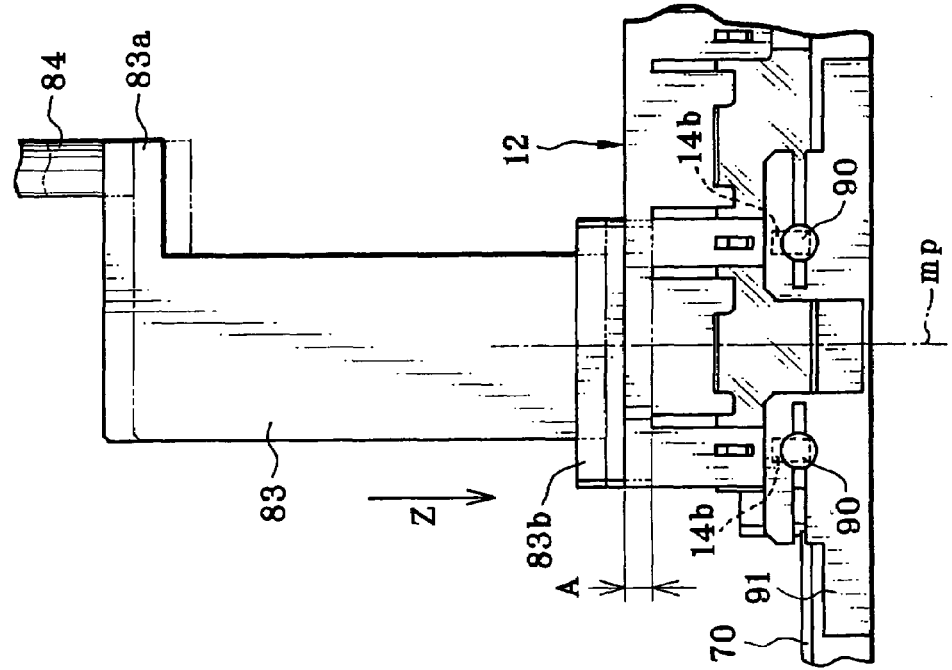
FIG. 8B is an explanatory view in elevation illustrating the same as FIG. 8A but with the pad moved away.

When the slider 81 shifts to the releasing position, the panel shaped movable pad 83 is away from the sensor unit 12 as illustrated in FIG. 8B. The Z axis pressing mechanism 71 shifts the movable pad 83 up and down, and presses the sensor unit 12 against the rail portion 70 to retain the same in the assay position mp. Also, the Z axis pressing mechanism 71 releases the sensor unit 12 from the pressure to set the sensor unit 12 movable by use of the handling head or pickup unit 64.

Specifically, the Z axis pressing mechanism 71 shifts the slider 81 in the holding position in a provisional manner, shifts back the slider 81 immediately to the releasing position, and then shifts the slider 81 in the holding position for the proper purpose. This is to hold the sensor unit 12 in the assay position mp by shifting the slider 81 from the releasing position to the holding position. Should the operation of holding be single, it is likely that the sensor unit 12 is held with an inclination upon occurrence of the inclination of the sensor unit 12 during movement toward the assay position mp. However, the provisional holding suggested in the embodiment is effective in eliminating the inclination of the sensor unit 12 so as to hold the sensor unit 12 in a proper orientation.

In FIG. 7, stationary pins or pad portions 90 are disposed in the Y axis clamping mechanism 72 and symmetrical with each other in relation to the assay position mp. A stationary board 91 keeps the stationary pins 90 fixed on the support 73. A pitch of the stationary pins 90 corresponds to the pitch of the erect surface 14b defined at the end faces of the sensor unit 12.

Figure 9:
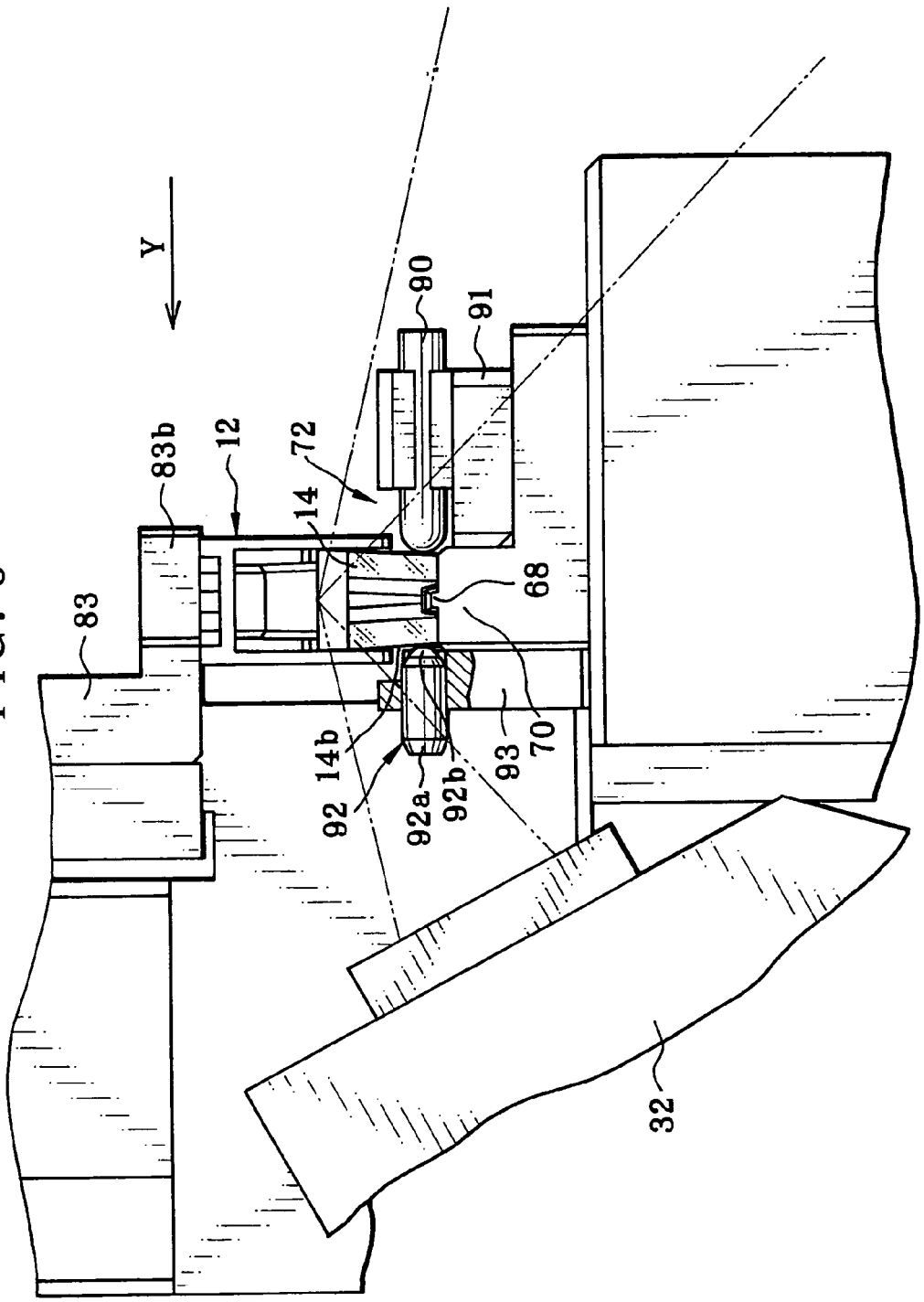
FIG. 9 is a side elevation, partially broken, illustrating a Y axis clamping mechanism.

In FIG. 9, pressure devices or spring plungers 92 or other suitable plunger mechanisms are incorporated in the Y axis clamping mechanism 72, and are opposed to respectively the stationary pins or pad portions 90 beside the rail portion 70. Each of the spring plungers 92 includes a case or plunger receptacle 92a and a plunger head 92b in a manner similar to the spring plunger 82 in the Z axis pressing mechanism 71. A spring (not shown) is contained in the plunger receptacle 92a and biases the plunger head 92b in a direction to protrude to the outside of the plunger receptacle 92a. A plunger holder 93 fixes each of the spring plungers 92 to the support 73.

A plunger head 91b has an end. An interval between the end and an end of the stationary pins or pad portions 90 is slightly smaller then a width of the sensor unit 12. When the sensor unit 12 is shifted to the assay position mp, the plunger head 91b comes to contact a lateral face of the prism 14, and retreats in the plunger receptacle 92a. The spring plungers 92 with the plunger head 91b retracted press the sensor unit 12 by means of bias of the spring inside the plunger receptacle 92a. Thus, the sensor unit 12 is squeezed in contact with the stationary pins 90.

The stationary pins or pad portions 90 and the spring plungers 92 are symmetrical with respect to the assay position mp. The Y axis clamping mechanism 72 holds sides of the sensor cells 17 as a target set in the assay position mp. The Y axis clamping mechanism 72 prevents offsetting of the sensor unit 12 in the direction of the Y axis, and prevents rotation of the sensor unit 12 about the Z axis and X axis. A pitch of the stationary pins 90 and of the spring plungers 92 corresponds to the pitch of the erect surface 14*b*. The Y axis clamping mechanism 72 clamps the erect surface 14*b* when the sensor cell 17 is set in the assay position mp. As the lateral faces of the prism 14 are inclined, unwanted upward force may occur should the inclined lateral faces be pushed. Forming of the erect surface 14*b* is for the purpose of preventing offsetting upon squeezing. The Y axis clamping mechanism 72 holds the erect surface 14*b* reliably to position the sensor unit 12 in the assay position mp. A reference surface is constituted by the erect surface 14*b*.

The sensor unit 12, when shifted to the assay position mp, is clamped by the Y axis clamping mechanism 72 at lateral faces, and also pressed against the rail portion 70 by the Z axis pressing mechanism 71. As the handling head or pickup unit 64 squeezes ends of the sensor unit 12, the sensor unit 12 in the assay position mp is kept fixed in the three directions of X, Y and Z. The Z direction of the Z axis pressing mechanism 71 is the first direction. The X direction of the pickup unit 64 is the second direction. The Y direction is perpendicular to each of the X and Z directions, and is the third direction.

In FIG. 4, a pipette head 75 with the multiple pipette assembly 26 is shifted by the dispenser shifter 52 in the directions of X, Y and Z. The dispenser shifter 52 is a moving device and may include a conveyor belt, pulleys, a carriage and a motor. Specifically, the dispenser shifter 52 includes a vertical moving unit, a Y axis moving unit and an X axis moving unit. The vertical moving unit shifts up and down the pipette head 75. The Y axis moving unit shifts the vertical moving unit together with the pipette head 75 in the direction Y. The X axis moving unit shifts the Y axis moving unit in the direction X with the vertical moving unit.

Pipette tips are fitted on ends of pipette nozzles of respectively the pipette devices 26*a* and 26*b* in a removable manner. The pipette tips are detipped for renewal so as to prevent mixture and contamination of plural liquids in the pipette tips because of direct contact with flowing liquid. The assay apparatus 11 includes a pipette tip storage (not shown) so positioned that the pipette head 75 in the casing 54 can access those, for storing the pipette tips for renewal.

A well plate 76 as reservoir is contained in the casing 54 for storing the analyte fluid 27. A panel 77 fixed on a side of the casing 54 supports the well plate 76. Wells in the well plate 76 store various examples of the analyte fluid 27. Various reservoirs (not shown) for fluids are disposed in positions where the pipette head 75 can access in the casing 54, the fluids including buffer for assay, washing fluid and the like. The dispenser shifter 52 causes the pipette head 75 to access the well plate 76 and fluid reservoirs, so the multiple pipette assembly 26 draws one of the fluids. After this, the pipette head 75 is shifted to the assay stage 53 for the multiple pipette assembly 26 to access the flow channel 16 in one of the sensor cells 17 set in the assay position mp, so the multiple pipette assembly 26 dispenses and aspirates fluid. Note that a dispenser is constituted by the pipette head 75 and the dispenser shifter 52.

Figure 10:
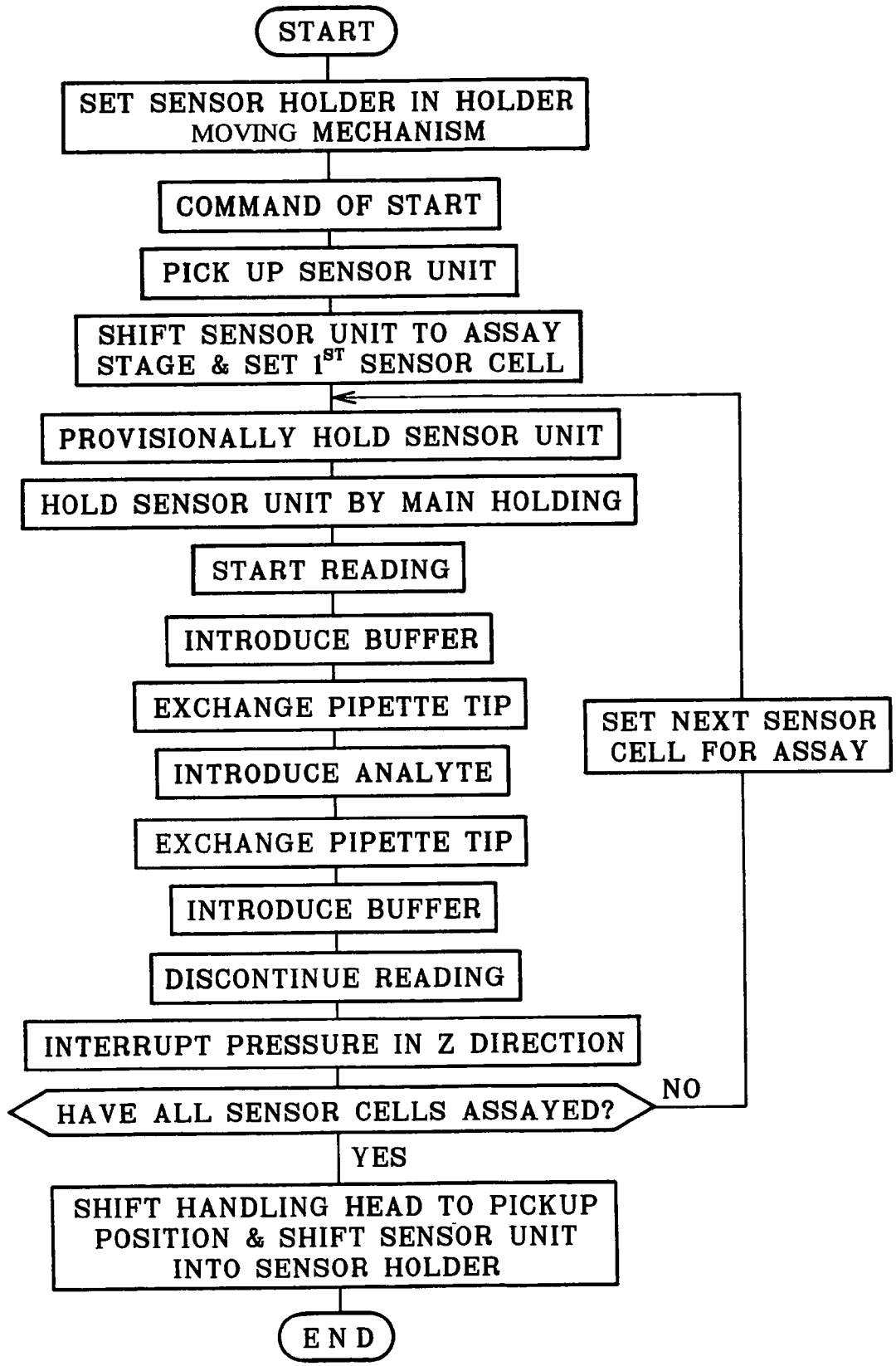
FIG. 10 is a flow chart illustrating a flow of the assay.

The operation of the assay apparatus 11 is described with reference to the flow in FIG. 10. For the assay, at first, the sensor unit 12 after the immobilization is contained in the sensor holder 45, which is set in the placing region 62 of the holder moving mechanism 50. A start command signal is input to start the assay of the assay apparatus 11.

The controller 55 drives the belt 60 in response to a start signal for the assay. The panel of the placing region 62 is shifted in the direction Y to shift up one of the sensor unit 12 of the sensor holder 45 to the ready position. The controller 55 then moves the handling head or pickup unit 64 to the pickup position. Then the first sensor shifter 63 is driven to raise the sensor unit 12 in the ready position up from the sensor holder 45.

When the sensor unit 12 is pushed up, the handling head or pickup unit 64 starts moving toward the assay stage 53. The pickup unit 64 then comes to squeeze the sensor unit 12 between the holding arms 206 and 207. The pickup unit 64 together with the sensor unit 12 moves to the assay stage 53, and sets a first one of the sensor cells 17 in the assay position mp, the first being the nearest to the assay stage 53. The controller 55 sends the stepping motor 67 pulses to shift the sensor unit 12 stepwise at a pitch of arrangement of the sensor cells 17. The sensor cells 17 become set in the assay position mp one after another for assay. It is possible to control the position of the sensor unit 12 according to the number of rotations of the stepping motor 67, or by use of a positioning sensor additionally disposed.

When the sensor cell 17 is set in the assay position mp, the controller 55 sends a pulse to the stepping motor 80 in the Z axis pressing mechanism 71, shifts the slider 81 from the releasing position to the holding position, to press the sensor cell 17 in the assay position mp against the rail portion 70. For this purpose, provisional holding and main holding are used. The controller 55 at first sets the slider 81 in the holding position, shifts back the same to the releasing position, and then shifts the slider 81 to the holding position. This eliminates an inclination from the sensor unit 12, and is effective in properly positioning the sensor unit 12.

The sensor unit 12 of which one of the sensor cells 17 is set in the assay position mp is squeezed by the Y axis clamping mechanism 72 laterally, and prevented from offsetting in the Y direction. The sensor unit 12 is squeezed by the handling head or pickup unit 64 longitudinally, and prevented from offsetting in the X direction. The sensor unit 12 in the assay position mp can be stably kept immovable in the X, Y and Z directions.

The sensor unit 12 being held by the Z axis pressing mechanism 71, the controller 55 starts the optical assay unit 31 to read data. At the same time, the controller 55 drives the dispenser shifter 52 to shift the pipette head 75 to a fluid reservoir (not shown). The pipette head 75 at the fluid reservoir causes the multiple pipette assembly 26 to aspirate buffer for assay. The pipette head 75 with the buffer shifts to the assay stage 53, and inserts the multiple pipette assembly 26 into the flow channel 16 of one of the sensor cells 17 set in the assay position mp for assay. In the multiple pipette assembly 26 accessing the flow channel 16, the pipette device 26*a* dispenses and introduces the buffer into the flow channel 16. The pipette device 26*b* aspirates and removes the buffer from the flow channel 16.

When dispensation and aspiration of buffer for measurement are completed, the pipette head 75 moves the multiple pipette assembly 26 up away from the flow channel 16. However, the sensor unit 12 is retained in all of the X, Y and Z directions, and can be kept firmly positioned even during the access of the multiple pipette assembly 26 to the flow channel 16. The Z axis pressing mechanism 71 presses the sensor unit 12 against the rail portion 70, so occurrence of a gap between the flow cells 41 and the prism 14 can be prevented upon removal of the multiple pipette assembly 26 from the flow channel 16. Thus, no fluid will leak even when the multiple pipette assembly 26 is moved away while the flow channel 16 is filled with the fluid.

The pipette head 75 after shifting the multiple pipette assembly 26 away from the flow channel 16 moves to a pipette tip storage (not shown), to exchange pipette tips at the end of the multiple pipette assembly 26. The pipette head 75 after the exchange shifts to the well plate 76, and causes the multiple pipette assembly 26 to draw the analyte fluid 27. The pipette head 75 with the analyte shifts to the assay stage 53, and inserts the multiple pipette assembly 26 into the flow channel 16 of one of the sensor cells 17 set in the assay stage 53. The analyte fluid is dispensed to and aspirated from the flow channel 16.

The pipette head 75 after the dispensation and aspiration of the analyte fluid 27 shifts to the pipette tip storage, to exchange the pipette tip. The pipette head 75 shifts to the fluid reservoir, causes the multiple pipette assembly 26 to draw the buffer for assay. The buffer is dispensed into, and then aspirated from, the flow channel 16 of a targeted one of the sensor cells 17. The optical assay unit 31 obtains the SPR signal in a process including detection of the base line or reference level, interaction between analyte and ligand, and introduction of buffer for assay to dissociate the analyte from the ligand. After the dispensation and aspiration of the buffer, the controller 55 interrupts reading of data in the optical assay unit 31. Thus, the assay of the first sensor cell 17 is completed.

After the assay of the first sensor cell 17, the controller 55 sends pulses to the stepping motor 80 of the Z axis pressing mechanism 71, to shift the slider 81 to the releasing position. The controller 55, upon interrupting pressure of the sensor unit 12 to the rail portion 70, sends pulses to the stepping motor 67 in the handling head driving unit 65 or X axis moving unit, to set a second one of the sensor cells 17 in the assay position mp. Similarly, the controller 55 effects assays with six sensor cells 17 in the sensor unit 12. The controller 55 after all of the sensor cells 17 moves the handling head or pickup unit 64 to the pickup position, to shift the sensor unit 12 after the assay back to the sensor holder 45.

Although the spring plunger 82 in the Z axis pressing mechanism 71 keeps the sensor unit 12 positioned on the rail portion 70 in the above embodiment, it is possible to press the sensor unit 12 against the rail portion 70 in a different manner. For example, the slider 81 is controlled for the position by use of the number of rotations of the stepping motor 80, to depress the flow cells 41 to deform elastically owing to its resilient material. In particular, an amount or depth of the deformation of the flow cells 41 can be preferably 0.3 mm or so.

In the above embodiment, the number of the time of the provisional holding of the Z axis pressing mechanism 71 is one. However, number of times of the provisional holding of the Z axis pressing mechanism 71 for the sensor unit 12 to the rail portion 70 may be two or more. Also, an additional sensor may be used for detecting an inclination or orientation of the sensor unit 12. It is possible to repeat or continue the provisional holding so as to ensure proper orientation of the sensor unit 12 according to an output of the sensor.

In the above embodiment, the stationary pins or pad portions 90 and the spring plungers 92 are included in the Y axis clamping mechanism 72. However, other structures can be used, for example a first pin, a second pin opposed to the first pin, and a sliding mechanism for sliding the first pin relative to the second pin. The interval between the pin can be changed to shift the sensor unit 12 between a first position of retention and a second position of release, for the purpose of squeezing in the Y direction. Any of various known structures can be used with the sliding mechanism, for example, a motor and a gear, and a solenoid.

In the above embodiment, a dielectric medium is the prism 14. However, a dielectric medium used in the invention may be a panel of an optical glass, a panel of an optical plastic material, and a composite structure including a prism, panels of any of those, and index-matching oil with which the prism and panels are fitted.

In addition to the SPR sensor, an assay sensor unit according to the invention can be other sensor in utilizing attenuated total reflection. One example of sensor unit according to utilizing the attenuated total reflection is a leaky mode sensor. The leaky mode sensor includes a dielectric medium, a cladding layer overlaid on the dielectric medium, and an optical waveguide layer overlaid on the cladding layer, those layers constituting a thin film. A first surface of the thin film is a sensing surface on the optical waveguide layer. A second surface of the thin film is a metal/dielectric interface on the cladding layer. When light becomes incident on the metal/dielectric interface to satisfy the condition of the total reflection, part of the light passes through the cladding layer, and enters the optical waveguide layer. A guided mode to propagate light is excited responsively in the optical waveguide layer, to attenuate the reflected light on the metal/dielectric interface. An angle of the incidence at which the guided mode is excited is changeable according to the refractive index of the medium positioned on the sensing surface. This is similar to the characteristic of the resonance angle of the SPR sensor. The attenuation of the reflected light is detected, so that it possible to measure the interaction on the sensing surface.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An assay apparatus for assay in utilizing attenuated total reflection, comprising:

an assay stage for being removably loaded with a sensor unit including a dielectric medium overlaid with a thin film, and a flow cell having a flow channel for flow of sample in contact with said thin film;

a dispenser, having a pipette device for accessing said flow channel of said sensor unit set in said assay stage, for dispensing and introducing said sample into said flow channel;

a light source for applying illuminating light to said thin film to satisfy a total reflection condition;

a photo detector for receiving said illuminating light reflected by said thin film, to convert said illuminating light into an electric output; and a pressing mechanism for pressing said sensor unit on said assay stage for holding in a first direction in which said pipette device is moved for access, wherein said sensor unit has a linker film capable of immobilizing ligands and which contains immobilized ligands which is overlaid on said thin film.

2. An assay apparatus as defined in claim 1, further comprising:

a placing region for receiving placement of said sensor unit prior to assay with said light source and said photo detector; and a sensor shifting mechanism for squeezing said sensor unit in said placing region in a second direction being substantially perpendicular to said first direction, and for setting said sensor unit in said assay stage.

3. An assay apparatus as defined in claim 2, further comprising a clamping mechanism for clamping said sensor unit on said assay stage in a third direction being substantially perpendicular to said first direction and to said second direction.

4. An assay apparatus as defined in claim 3, wherein said sensor unit includes plural sensor cells, arranged in a sensor cell train in said second direction, and respectively having said flow channel and said thin film;

said sensor shifting mechanism squeezes said sensor unit in said second direction, and shifts said sensor unit in said second direction, selectively to set said sensor cells in an assay position being within a light path from said light source.

5. An assay apparatus as define a in claim 4, wherein said sensor unit has a reference surface being substantially perpendicular to said third direction, and is clamped by said clamping mechanism on said reference surface.

6. An assay apparatus as defined in claim 5, wherein said clamping mechanism includes:

a stationary pin portion stationary on said assay stage; and a spring plunger, opposed to said stationary pin portion, for pressing said sensor unit on said stationary pin portion.

7. An assay apparatus as defined in claim 2, wherein said sensor shifting mechanism includes:

a pickup unit, having first and second holding arms, for squeezing said sensor unit in said second direction between; and a moving unit for moving said pickup unit in said second direction.

8. An assay apparatus as defined in claim 7, wherein said pickup unit includes:

a first pickup block for supporting said first holding arm;

a second pickup block, secured to said first pickup block in a slidable manner, for supporting said second holding arm; and a biasing portion for biasing at least one of said first and second pickup blocks in a direction to come nearer to each other.

9. An assay apparatus as defined in claim 1, wherein said pressing mechanism includes:

a movable pad having a contact portion for contacting said sensor unit;

a moving unit for moving said pad to press said sensor unit; and a spring plunger for adjusting pressure of said pad to said sensor unit.

10. An assay apparatus as defined in claim 9, wherein said contact portion includes a through hole or recess for enabling access of said pipette device to said flow channel while said sensor unit is pressed on said assay stage.

11. An assay apparatus as defined in claim 1, wherein said pressing mechanism, prior to holding said sensor unit in a main holding step, presses said sensor unit on said assay stage for at least one time, and shortly discontinues pressing of said sensor unit.

12. An assay apparatus as defined in claim 1, wherein said assay stage includes:

a support for supporting said light source and said photo detector;

a rail portion, secured to said support, for receiving a lower surface of said sensor unit, and for keeping said sensor unit slidable while said sensor shifting mechanism shifts said sensor unit;

wherein said pressing mechanism contacts an upper surface of said sensor unit for pressing said sensor unit on said rail portion.

13. An assay method of assay in utilizing attenuated total reflection, wherein an assay stage is removably loaded with a sensor unit including a dielectric medium overlaid with a thin film, and a flow cell having a flow channel for flow of sample in contact with said thin film, and said assay stage includes a light source for applying illuminating light to said thin film to satisfy a total reflection condition, and a photo detector for receiving said illuminating light reflected by said thin film, to convert said illuminating light intro an electric output, and a pipette device is caused to access said flow channel of said sensor unit set in said assay stage, for dispensing and introducing said sample into said flow channel, said assay method comprising steps of:

pressing said sensor unit on said assay stage for holding in a first direction in which said pipette device is moved for access;

wherein said sensor unit has a linker film capable of immobilizing ligands and which contains immobilized ligands; and while said sensor unit is pressed in the main holding step, introducing said sample into said flow channel by setting said pipette device, to measure reaction of said sample with immobilized ligands on said thin film.

14. An assay method as defined in claim 13, further comprising, prior to said main holding step:

pressing said sensor unit one or more times, as a provisional holding step, to orient said sensor unit on said assay stage, and discontinuing said pressing.

15. An assay method as defined in claim 13, further comprising, prior to assay with said light source and said photo detector:

squeezing said sensor unit in a second direction being substantially perpendicular to said first direction, and thereby setting said sensor unit in said assay stage;

wherein during assay, said sensor unit is kept pressed on said assay stage in said first direction, and kept squeezed in said second direction.

16. An assay method as defined in claim 15, further comprising:

clamping said sensor unit on said assay stage in a third direction being substantially perpendicular to said first direction and to said second direction.

* * * * *